United States Patent [19]
Livingston

[11] Patent Number: 4,475,399
[45] Date of Patent: Oct. 9, 1984

[54] APPARATUS FOR ULTRASONIC TESTING OF TUBULAR GOODS

[76] Inventor: Waylon A. Livingston, 2534 Hollywood, Norman, Okla. 73069

[21] Appl. No.: 407,137

[22] Filed: Aug. 11, 1982

[51] Int. Cl.³ .......................................... G01N 29/04
[52] U.S. Cl. ...................................... 73/622; 73/637; 73/638
[58] Field of Search .......................... 73/622, 637, 638

[56] References Cited

U.S. PATENT DOCUMENTS

| | | | |
|---|---|---|---|
| 3,593,569 | 7/1971 | Wilson | 73/622 |
| 3,868,847 | 3/1975 | Gunkel | 73/622 |
| 3,955,425 | 5/1976 | Corneau | 73/622 |
| 3,958,451 | 5/1976 | Richardson | 73/622 |
| 3,981,184 | 9/1976 | Matay | 73/622 |
| 4,106,347 | 8/1978 | De Kerlegand | 73/622 |

FOREIGN PATENT DOCUMENTS 2806550 8/1979 Fed. Rep. of Germany ........ 73/622

*Primary Examiner*—Howard A. Birmiel
*Attorney, Agent, or Firm*—Robert M. Hessin

[57] ABSTRACT

Apparatus for ultrasonic flaw inspection of non-rotating tubular goods. The apparatus includes a test head with circumferential arrays of transducers oriented for inspection for each of transverse, longitudinal and wall thickness defects, and the test head includes individual pulser and pre-amplifier arrays as sequentially controlled from a remotely disposed operator console. The console includes sequential signal processing circuitry for developing and displaying defect indications for the test specimen as it is moved longitudinally through the test head. The signal processing circuitry includes separate processing channels for each of the transverse, longitudinal and wall thickness transducers, and each channel includes receiver, gate processing and average counter circuitry which develop data signals for output to selected chart and monitor scope indicators.

14 Claims, 18 Drawing Figures

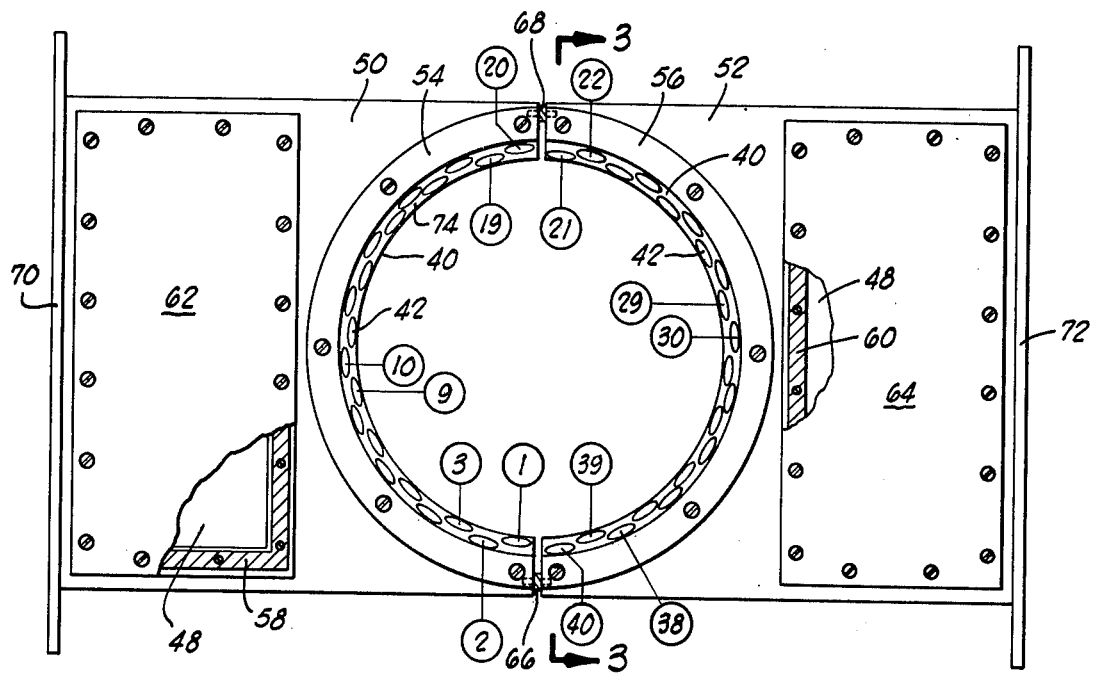
FIG. 2
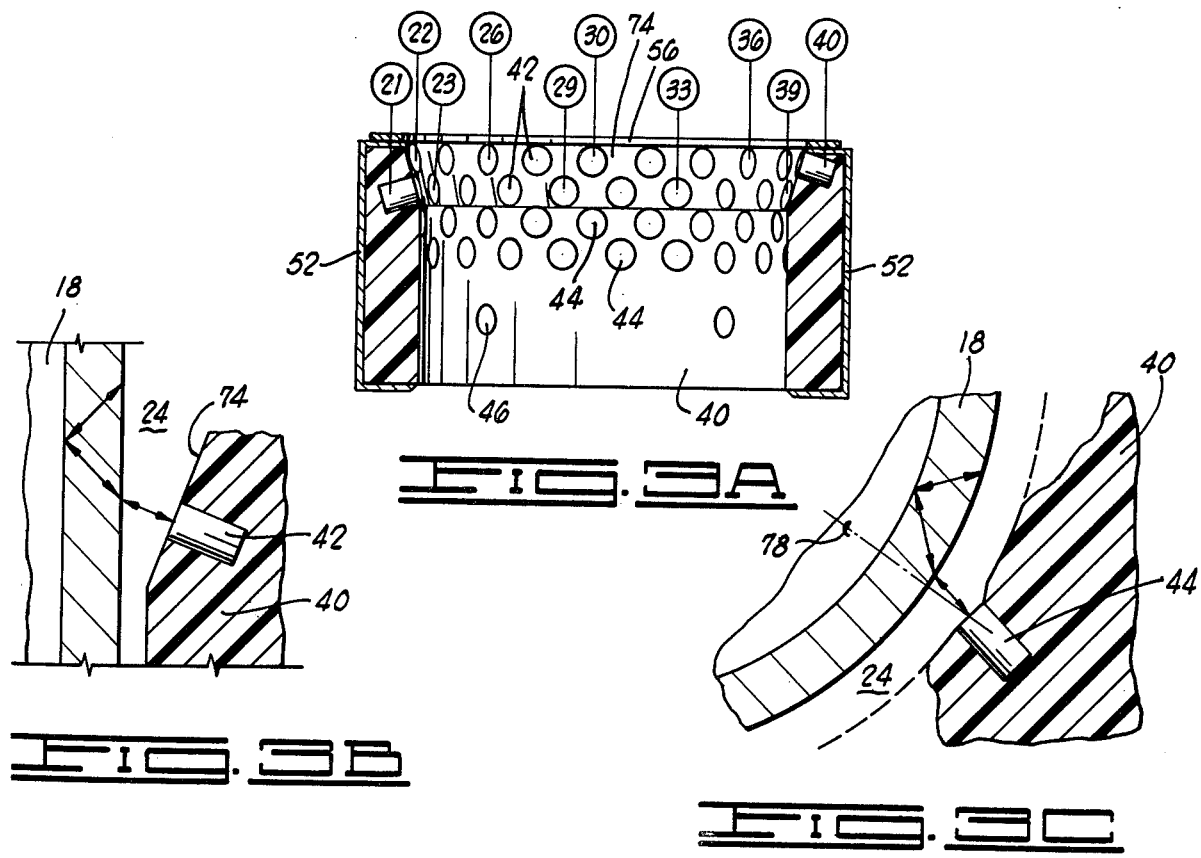
FIG. 3A
FIG. 3B
FIG. 3C

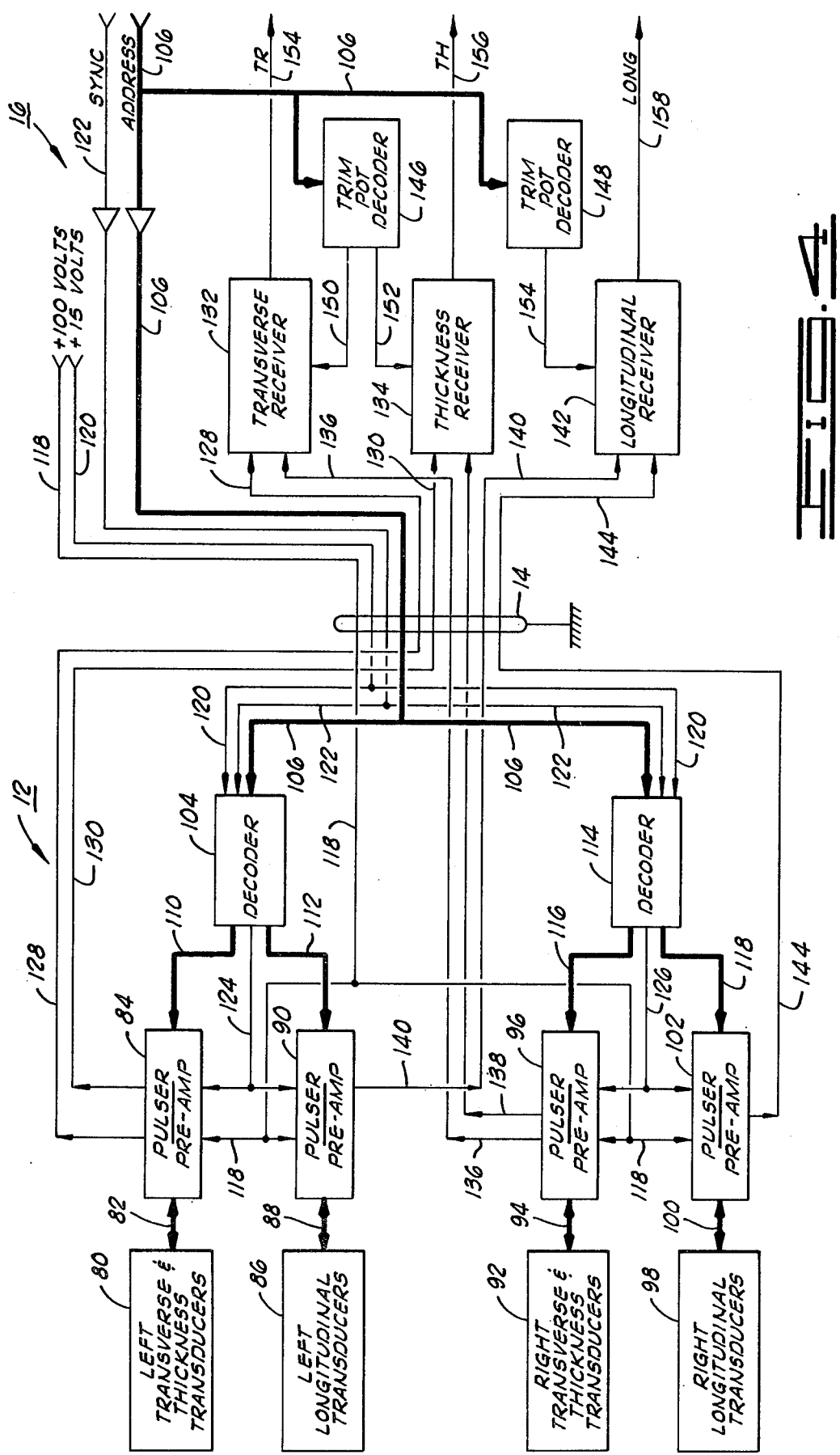

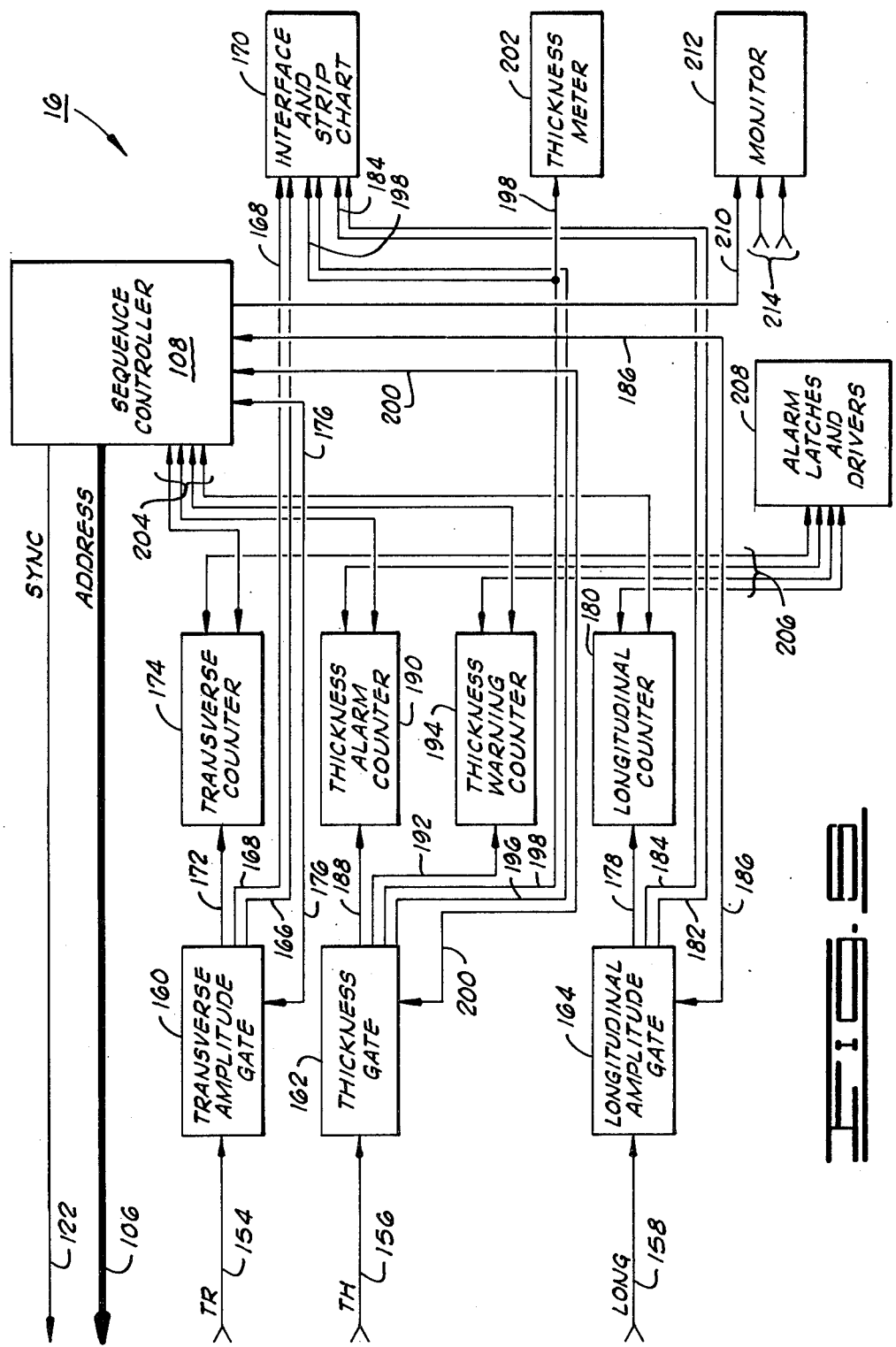

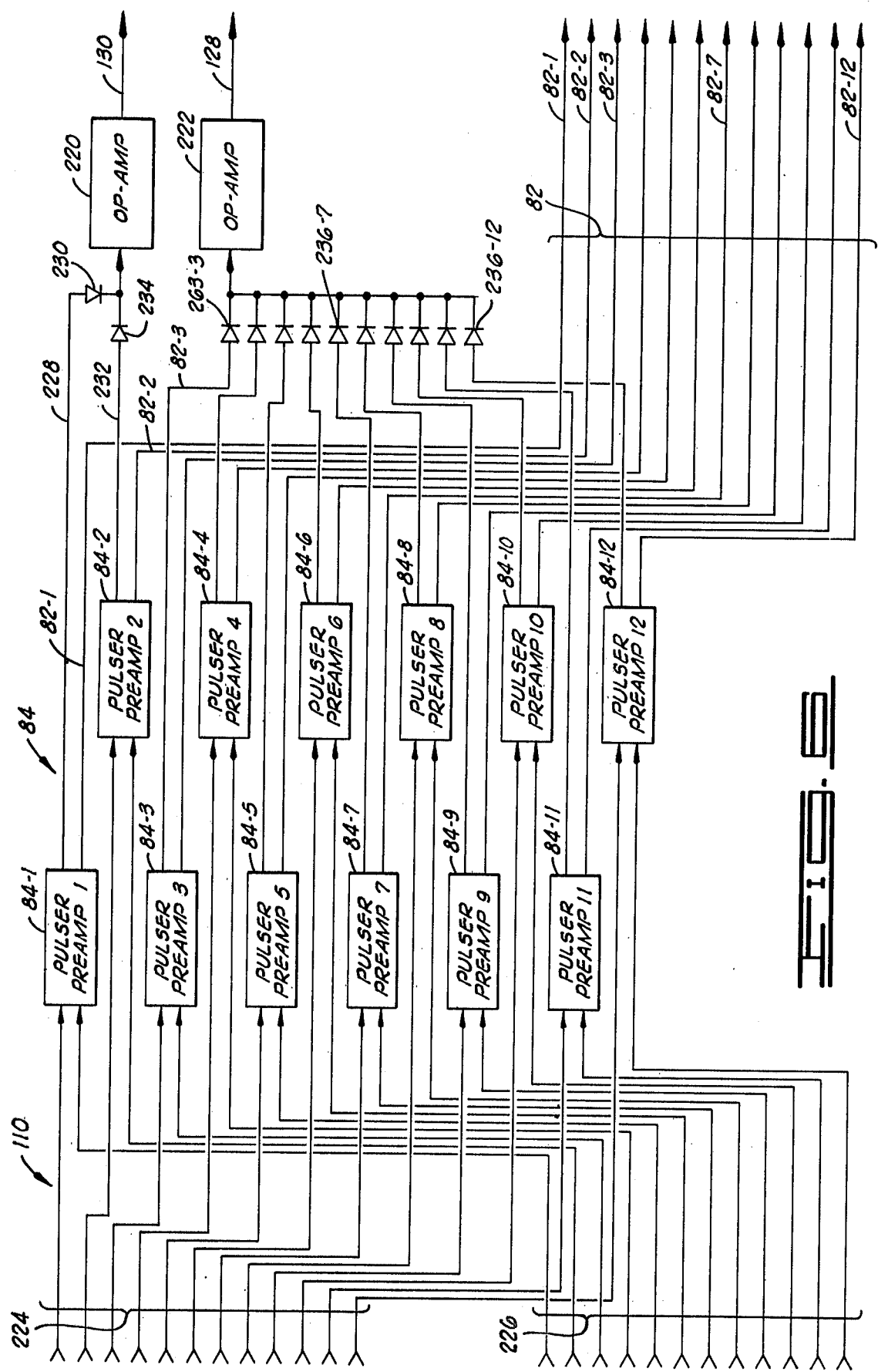

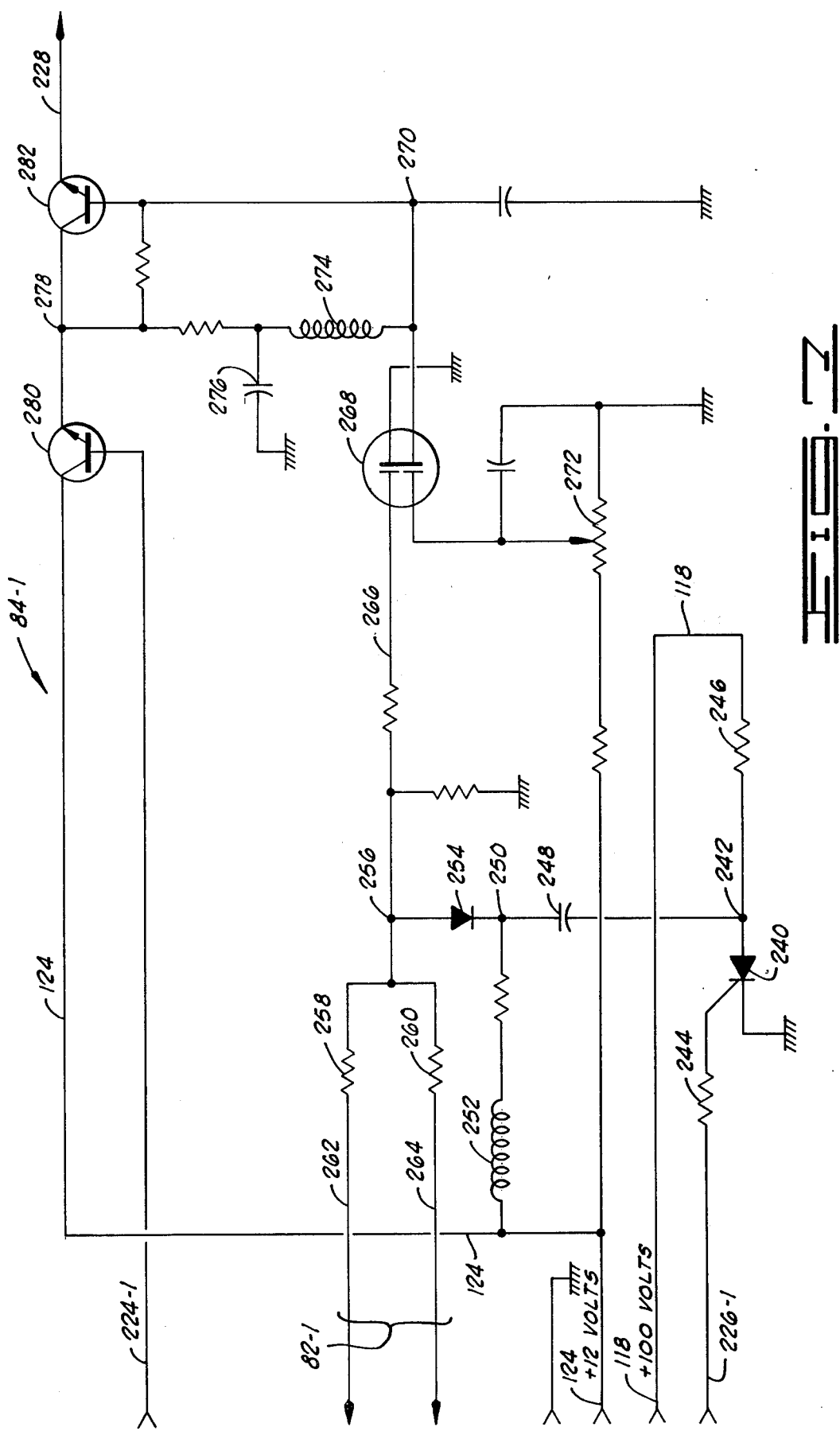

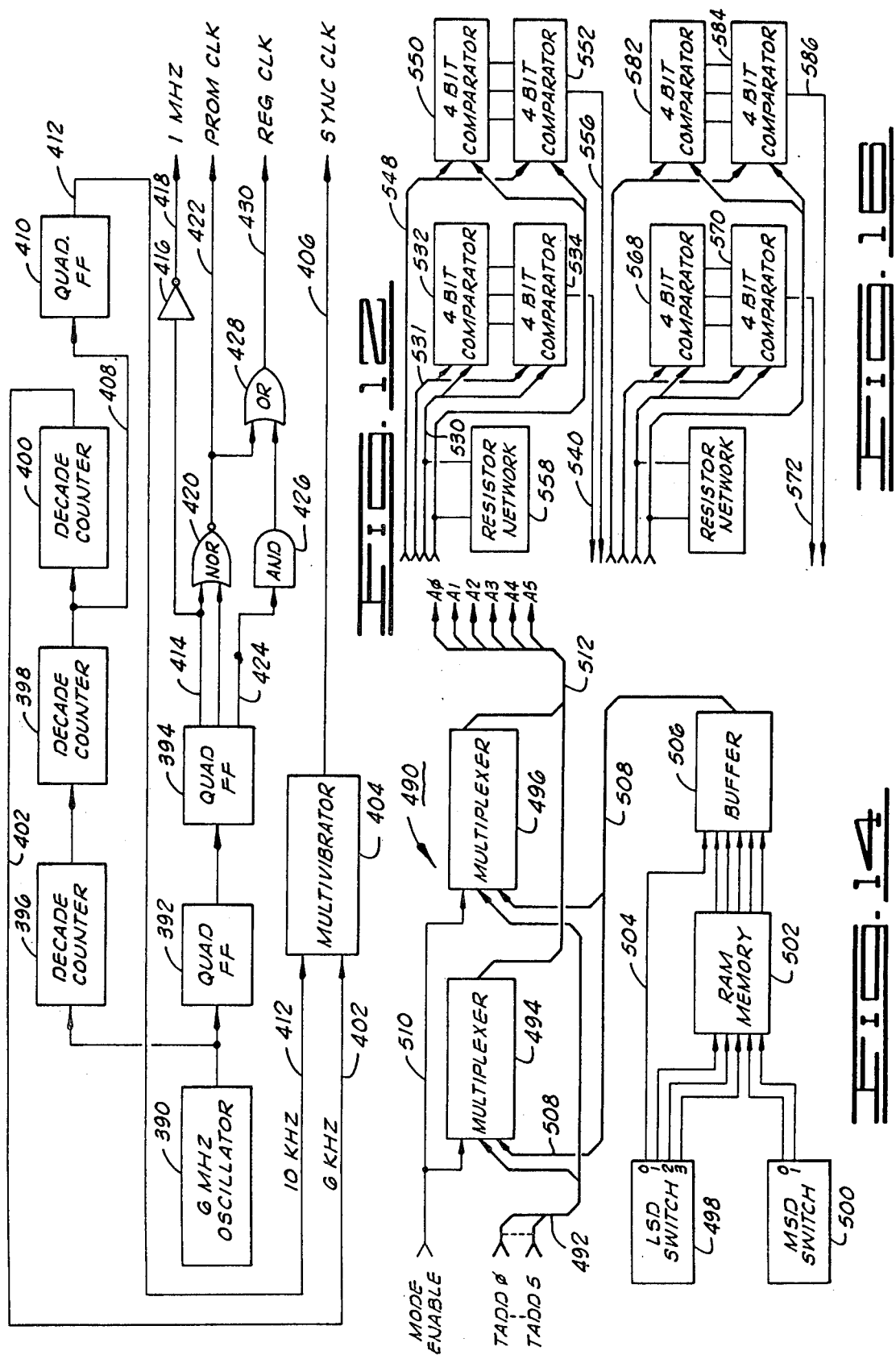

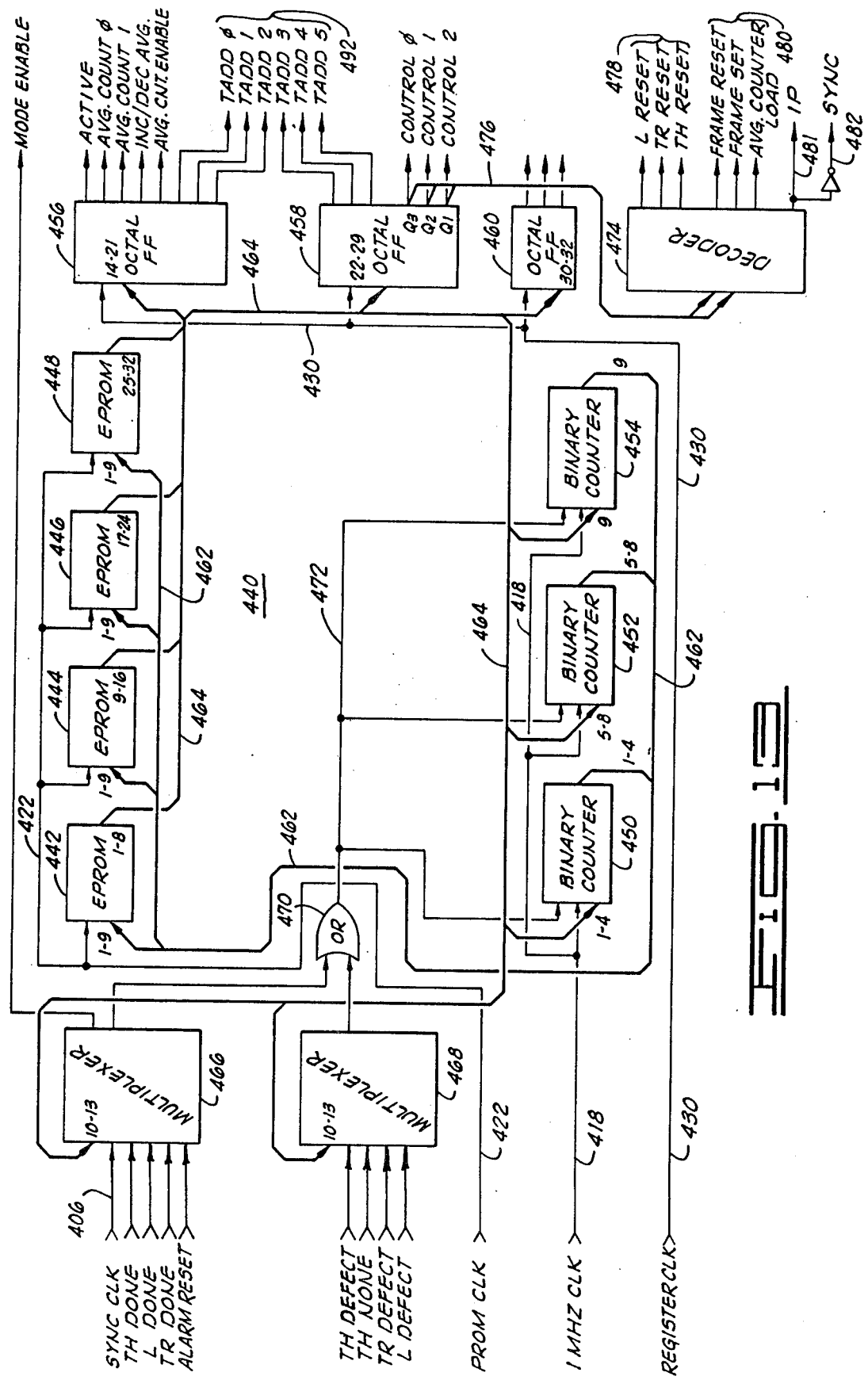

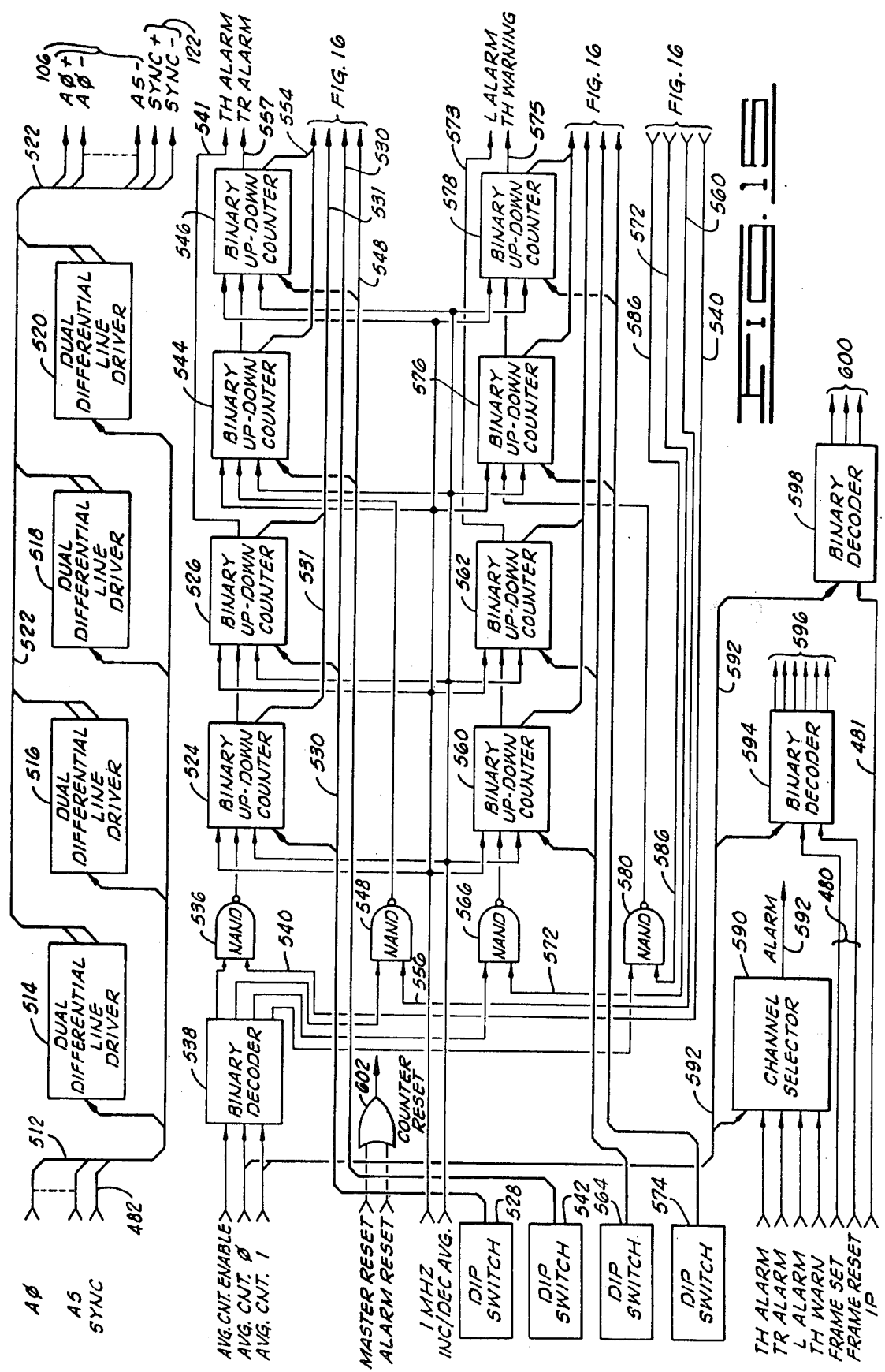

APPARATUS FOR ULTRASONIC TESTING OF TUBULAR GOODS

BACKGROUND OF THE INVENTION

1. Field of the Invention

The present invention relates to improvements in method and apparatus for ultrasonic testing of tubular goods to determine defects, defect orientation and continuity, as well as wall thickness and, more particularly, but not by way of limitation, it relates to improvements in ultrasonic inspection apparatus which enables continuous circumferential testing without rotation of the tubular goods specimen.

2. Description of the Prior Art

The prior art includes various types of apparatus for ultrasonic testing of homogenous material, sheet or rod stock, with some more recent developments attempting such as continuous surface inspection of tubular goods. In most prior art attempts at ultrasonic inspection of tubular goods, it has been necessary to rotate the tubular goods specimen at a prescribed rate relative to its longitudinal movement past ultrasonic testing heads in order to provide complete and reliable surface coverage of the specimen wall or body. Most recently, there have been attempts at full and complete ultrasonic testing of tubular goods at acceptable linear inspection rates without requiring rotation of the specimen. U.S. patent application Ser. No. 242,833 as filed on Mar. 12, 1981 and entitled "Method and Apparatus for Ultrasonic Testing of Tubular Goods" in the name of the present inventor, discloses one form of circumferential testing apparatus wherein each of transverse and longitudinal defects can be ascertained, and periodic wall thickness measurement may be taken as well. The apparatus of U.S. application Ser. No. 242,833 is particularly adapted for on-site inspection of oil well drilling tubular goods during its tripping or vertical attitudes, although the same system is readily adapted for various horizontal testing applications in either field operational or manufacturing facilities.

Other prior art to be considered should include German Pat. No. 28 06 550 as filed on Feb. 16, 1978 as this reference teaches an approach to circumferential ultrasonic inspection utilizing a peripheral alignment of plural ultrasonic sensors with each having sufficient arcuate coverage to provide complete circumferential coverage of the tubular specimen. This is achieved by using two peripheral transducer arrays of equal sectoral coverage but staggered in an equal offset alternating relationship. The pair of arrays may be disposed adjacent one another, but each transducer array must be individually adjusted through a transducer lens and positioning device relative to the particular tubular goods specimen. If both transverse and longitudinal defect detection is desired, then it is necessary to align and adjust a separate pair of circumferential arrays for each of the selected defect characteristics. This reference contemplates no specific electronic apparatus for further differentiating types of defects or for wall thickness considerations.

British Pat. No. 2,027,199 (A) teaches the use of a number of precision ground convex ancillary lenses that are each focused in a highly restricted area. Pairs of transducers with lenses may be used in a pitch-catch mode such that a greater number of transducers are required to provide complete circumferential coverage. The specific teaching of the patent for testing up to 10 centimeter tube diameters uses six pitch/catch transducers in a peripheral array, and at least four such peripheral arrays are aligned in longitudinal juxtaposition but incrementally circumferentially offset each to the other in order to provide complete coverage. While mention is made that transverse defects and wall thickness measurements are possible, no teaching or alternative suggestions are present. Finally, yet another pitch/catch mode of circumferential tubular goods inspection is present in a publication entitled "A High-Speed Ultrasonic Testing Machine for Tubes", The Radio and Electronic Engineer, Volume 41, No. 5, May 1971, in the name of Kyte and Whittington. This teaching uses a series of identical probes arranged in a ring encircling the tubular goods, each individual energy path including a transmitter and receiver position, and fast sequential pulsing of the probes together with slow rotation of the tube will enable effective circumferential scanning. This teaching contemplates both twin-probe or pitch/catch mode and the transceiver mode of operation but there is still required the rotation of the tubular specimen, albeit at a slow rate. Also, utilizing the disclosed forms of array, it is emphasized that the outer limit of ultrasonic transducer employment in the single system would be less than 72, and that the largest tube size for practical application of testing is less than four inches outside diameter.

SUMMARY OF THE INVENTION

The present invention relates to improvements in ultrasonic inspection of tubular goods and is particularly directed to a full coverage transducer collar for longitudinal, transverse and thickness testing to provide a more definitive and more reliable readout of defect type and orientation, and the invention is particularly adapted for use on-site during vertical tripping and pipe handling operations to test oil well drilling tubular goods. The apparatus consists of a circumferential transducer array operative within a couplant bath at the tubular goods inspection site. Individual pulser and pre-amp circuitry is retained in water proof enclosure in close proximity at the testing site while the entire test head unit is connected by a multi-conductor umbilical cable to an operator control position and control console which may be located at a considerable distance. The test head unit transducers are sequentially pulsed singly or in selected groups for each of the transverse, longitudinal and thickness testing transducers and each, in turn, provides a sequential RF signal output pre-amplified for transmission to the control console. The control console includes an individual receiver and decoder for each of the longitudinal, transverse and thickness RF signals as each provides a video output signal to a respective gate circuit which further provides output to a respective averager circuit for alarm output. Each circuit output is also applied from the individual gates to a strip chart or other output recorder. Coordination of the signal multiplexing as between the individual transducer pulsing and output sequences is carried out by a microprocessor circuit having buss connection both to the receiver and decoder circuits and the pulser and pre-amp circuits within the test head unit.

Therefore, it is an object of the present invention to provide an ultrasonic testing device for non-rotated tubular goods which provides more complete and reliable tube wall surface coverage to ascertain each of transverse and longitudinal defects as well as wall thickness.

It is also an object of the present invention to provide an ultrasonic tester having the capability of distinguishing the size and orientation of defects.

It is still further an object of the present invention to provide an ultrasonic tester which is rig-safe and operative in hazardous environment as all pulser/pre-amp components and transducer interconnection are immersed within couplant bath at the testing site.

It is yet another object of the present invention to provide an ultrasonic test head for extended surface coverage which is capable of being located at considerable distances from the main control console without deleterious effects.

It is also an object of this invention to provide a circular array of testing transducers which provide full circumferential coverage of tubular goods within widely varying diametric limits without individual transducer or array adjustment.

Finally, it is an object of the present invention to provide an electronic multiplexing and processing system for use in ultrasonic testing of tubular goods which is maximum effective yet extremely rugged and of high reliability in operation in difficult environs such as those of an oil well drilling rig.

Other objects and advantages of the invention will be evident from the following detailed description when read in conjunction with the accompanying drawings which illustrate the invention.

BRIEF DESCRIPTION OF THE DRAWINGS

FIG. 2 is a top plan view of the test head unit with parts shown in cutaway;

FIG. 3A is a vertical section of the transducer array as taken through lines 3—3 of FIG. 2;

FIG. 3B is a view in partial vertical section of a transverse defect transducer within the array;

FIG. 3C is a view in partial horizontal section of a longitudinal defect transducer within the array;

FIG. 4 is a partial block diagram of the ultrasonic testing system showing the electronics within the head unit as connected by umbilical cable to the receiver section of the control console;

FIG. 5 is a continuation of the system block diagram of FIG. 4 showing the microprocessor and the gating, averaging, alarm and indicator sections of the control console;

FIG. 6 is a schematic wiring diagram of a single pulser/pre-amp circuit, four of which are illustrated in FIG. 4;

FIG. 7 is a schematic diagram of a single pulser pre-amp circuit, a plurality of which are illustrated in FIG. 6;

FIG. 12 is a block diagram of the clock circuitry of the sequence controller;

FIG. 13 is a block diagram of the control processor circuitry of the sequence controller;

FIG. 14 is a block diagram of the address circuitry of the sequence controller;

FIG. 15 is a block diagram of the counter circuitry which functions in co-action with the sequence controller; and FIG. 16 is a block diagram of comparator circuitry of the sequence controller.

DETAILED DESCRIPTION OF THE INVENTION

Figure 1:
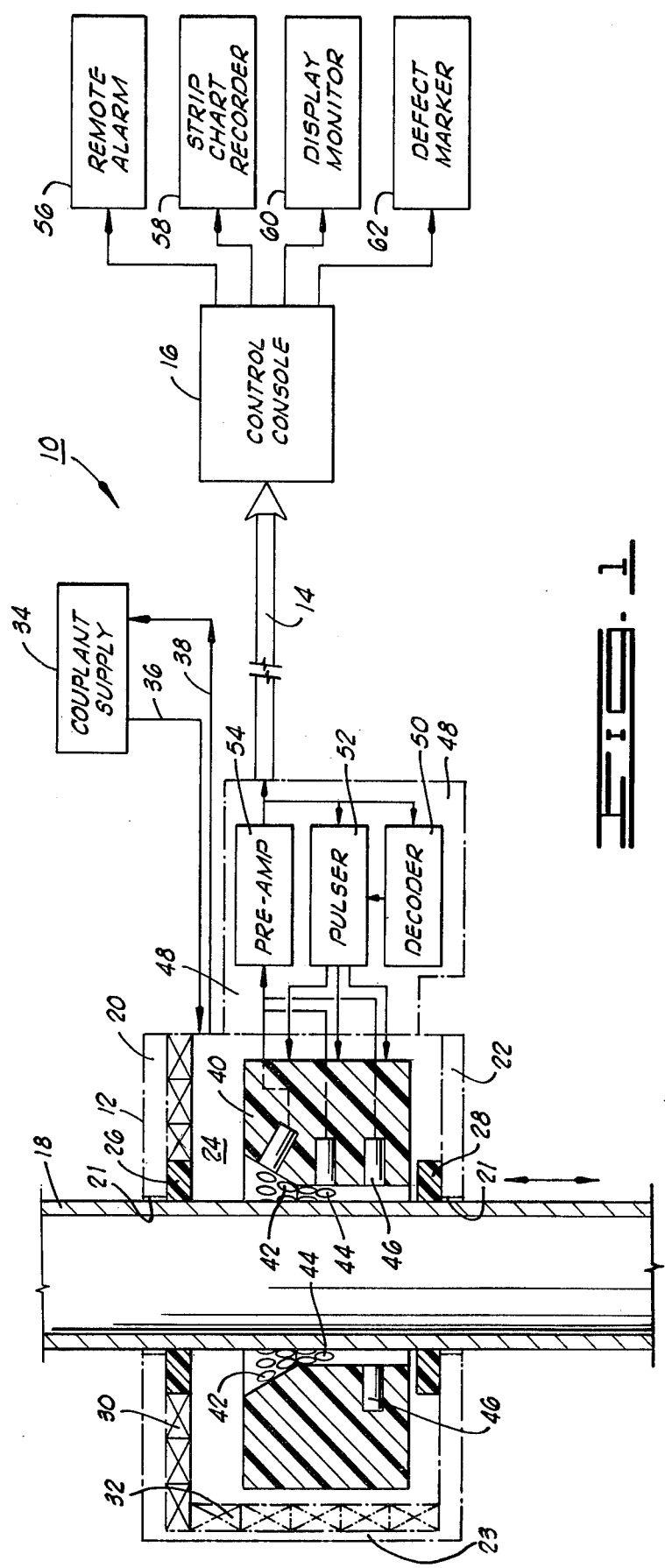
FIG. 1 is a block diagram with parts shown in section of the basic ultrasonic test head unit within the couplant frame as interconnected with the control console.

Referring to FIG. 1, an ultrasonic inspection system 10 consists of a test head unit 12 in connection via cable 14 to a control console 16. The test head unit 12 is suitably mounted at the test site for testing of tubular goods specimens such as pipe 18. Thus, and as more fully developed in Applicant's co-pending application Ser. No. 242,833, in one form of application, the test head units 12 may be supported below or above a drilling rig platform in operative testing position during drilling and tripping operations. However, the system may be utilized in diverse surrounds for testing of numerous types of tubular goods.

The test head unit 12 is comprised essentially of an outer metal couplant frame, e.g. aluminum, consisting of an upper plate 20, lower plate 22 and suitable water proof side plates 23. The central passage 21 is provided through upper and lower plates 20 and 22, and the resilient sealing means 26 and 28 serve to retain couplant while aligning the pipe 18, as fully set forth in the co-pending application Ser. No. 242,833. In addition, it has been found that an acoustically insulative damping member placed within the upper extremity of the couplant fluid 24 serves to greatly reduce extraneous couplant compression wave noise as picked up by the pulsers and eventually transmitted in the RF content to control console 16. Thus, a panel of vulcanized horsehair matting 30 is secured across the upper extremity of the fluid chamber or couplant 24 when test head unit 12 is used in the vertical testing attitude and, alternatively, if unit 12 is used in the horizontal testing mode then an insulative matting 32 would be suitably disposed along the uppermost surface of couplant chamber 24.

Circulation of suitable couplant, such as pre-lube, synthetic oil or the like, under low pressure is provided from a suitable couplant supply 34 through circulation lines 36 and 38 to the couplant chamber 24. The couplant may be heated and thermostatically maintained at supply 34 thereby to enable more effective all weather usage. A transducer array 40, including a circumferal array of transverse transducers 42, longitudinal transducers 44 and the quadrature arrayed thickness transducers 46, is suitably supported generally centrally within the couplant chamber 24 in operative alignment with axial ports 21. Transducers 42, 44 and 46 are conventional ultrasonic transducers, e.g. lead titanate.

As will be further described, the transducer array 40 is effectively supported within a rigid frame (see FIG. 2) which also defines a pair of waterproof circuit chambers 48 on either side of array 40. The chambers 48 as disposed on opposite sides of array 40 provide space for clip-in mounting of a plurality of pre-amp/pulser and decoder printed circuit boards which function to control the respective transducers in each half of array 40. Thus, in each half of array 40 which would include twenty transverse transducers 42, twenty longitudinal transducers 44, and two thickness transducers 46, the respective chamber 48 would include a decoder board 50 (FIG. 1) and two pulser/pre-amp boards 52-54 in coative interconnection with their respective transducers.

Incoming sync signal as well as decoder buss information and the RF signal output information are transmitted via umbilical cable 14 back to the control console 16 wherein the sequential multiplex signal information is processed and analyzed for output to provide display indication. Thus, an output is provided for actuating a remote alarm 56 and additional outputs are provided to a strip chart recorder 58 as well as a display monitor 60, e.g. a real time oscilloscope. Certain defect indications are also utilized to actuate a solenoid driven defect marker 62 which provides an optically discernible mark on the test specimen.

FIGS. 2 and 3 illustrate a particular form of array 40 as presently constructed to provide full circumferal coverage of an entire range of pipe diameters, e.g. 3½" OD to 6⅝" OD, to provide indication of all transverse and longitudinal defects as well as wall thickness. The array 40 is supported in two separable half sections by rigid frame members 50 and 52 which define respective opposite board housing chambers 48. The opposite halves of array 40 are sealingly secured within the respective frame members 50 and 52 as respective Delrin seals and sealing rings 54 and 56 are secured around the upper circumfery. Circuit board chambers 48 are sealingly secured by Delrin seals 58 and 60 as secured by respective cover plates 62 and 64. A suitable latch or hinge mechanism 66 and 68 provides attachment of the array frame members 50 and 52, and opposite side plates 70 and 72 provide mounting affixture within test head unit 12.

The particular transducer array 40 is constructed with eighty defect transducers 42 and 44 and four quadrature-arrayed wall thickness transducers 46 disposed therebelow. Referring also to FIG. 3A, an upper bevel surface 74 is formed at an angle of 19.75 degrees to the array axis of inner diameter wall 76 and forty transverse defect transducers 42 are rigidly secured thereabout, each radially aligned relative to the inner diameter of array 40 but directing energy at an angle of 19.75 degrees relative to the radius of array 40. Thus, as shown in FIG. 3B, reverberating acoustic energy within the wall of the test specimen 18, i.e. between the inner and outer diameter walls, will move upward with progressive lesser power reflections so that sensed energy will indicate homogeneous discontinuities lying transverse to the tubular goods axis.

Upper and lower rows of transverse transducers 42 are provided with twenty equally-spaced transducers each disposed in equal overlap so that the entire circumferal tube surface passing therethrough will receive ultrasonic energy input. Referring again to FIGS. 2 and 3A, the two rows of transverse transducers 42 are numbered sequentially progressing from No. 1 clockwise through Nos. 20 and 21 to terminate at No. 40. Under control of the associated pulser boards 52 (FIG. 1), the transverse transducers 42 are pulsed in pairs, each pair being displaced exactly ninety degrees in the array. Thus, the transducer pulsing sequence is as follows: pulse No. 1 fires transducers 1 and 11, pulse No. 2 fires transducers 2 and 12, pulse No. 3 fires transducers 3 and 13, and so on through pulse No. 11 firing transducers 21 and 31, pulse No. 12 firing transducers 22 and 32, and, finally, pulse No. 20 firing transducers 30 and 40.

Referring to FIGS. 3A and 3C, longitudinal defect transducers 44 are disposed in two equally-spaced and equally offset or staggered rows immediately beneath the bevel surface 74 around the inner diameter of array 40. Thus, forty transducers 44 are disposed in equal offset two-row array and numbered similarly to the transducers 42, and each longitudinal transducer 44 is directed at a similar slant angle or offset of 0.8190 inches relative to the array radius. As shown in FIG. 3C, each successive transducer 44 is viewing at a desirable refractive angle within the interior of the specimen wall, i.e. between ID and OD, and traversing enough specimen wall area to define a longitudinally aligned defect or inhomogeneity in the material. Pulsing of the transducers 44 takes place in ninety degree displaced pairs with numbering and succession the same as that for the transverse transducers 42, as above described. The thickness transducers 46 are also pulsed in selected sequence and directed radially into the tubular goods wall to provide a wall thickness travel time indication for conversion to thickness output.

While the specific transducer array of FIGS. 2 and 3 states the use of 84 transducers in circumferal array, it should be understood that there is a great degree of choice in selection of number and position of transducers for different sensing operations. Thus, the circuitry has the capability for firing up to 240 transducers and even higher since the decoders can trigger two or more transducers simultaneously and the particular pulser assemblies are capable of triggering a plurality of three or more transducers simultaneously. Thus, utilization of 240 or more transducers provide the proportionally greater and more detailed coverage of a circumferal surface and such magnified response characteristic is particularly desirable for inspection of larger sizes of pipe or tubing as they provide a greater density of coverage per circumfery. Non-interfering simultaneous firing of pluralities of pulsers can be effected simply by separating the arcuate positioning of the transducers within a firing group.

Referring now to FIG. 4, the left side transverse and thickness transducers 80 are connected via a plurality of pulser leads 82 to a pulser/pre-amp 84. The left transducers 80 include twenty transverse transducers 42 and two thickness transducers 46 and the pulser/pre-amp 84 is a printed circuit board including twelve pulser and pre-amplifier circuits and two operational amplifier circuits, as will be further described. Left longitudinal transducers 86 are connected through pulser leads 88 to a pulsar/pre-amplifier 90. In like manner, right transverse and thickness transducers 92 are connected to pulser leads 94 and pulser/pre-amplifier 96, and the right longitudinal transducers 98 are connected through pulser leads 100 to a pulser/pre-amplifier 102.

The left side transducers are pulsed under sequence controlled by a decoder 104 which receives address buss data input on line 106 from the sequence controller 108 (FIG. 5). The address data is contained on six pairs of leads $\pm A_0$ through $\pm A_5$, a conventional coding form, and decoder 104 responds to provide selective trigger outputs on select-trigger leads 110 and 112 to the respective pulser/pre-amps 84 and 90. Again in like manner, right side transducer firing is accomplished as a decoder 114 responds to address buss input on line 106 to provide firing output on trigger leads 116 and 188 to respective pulser/pre-amps 96 and 102.

A transducer firing voltage of positive 100 volts is generated at control console 16 and is transmitted via lead 118 through cable 14 for input to each of the pulser/pre-amplifiers 84, 90, 96 and 102. A +15 volt supply is provided by lead 120 through cable 14 and input to each of decoders 104 and 114 wherein it is to provide a regulated +12 volt source. Synch voltage, as generated in sequence controller 108, is output on lead 122 (FIG. 5) through cable 14 for input to each of decoders 104 and 114. Decoder 104 and 114 each provide a regulated +12 volt output on leads 124 and 126 to their respective pulser/pre-amplifiers 84, 124 and 96, 102. Transverse and thickness outputs in the form of an RF energy pulse are provided on respective leads 128 and 130 for conduction back through umbilical cable 14 for input to the transverse receiver 132 and thickness receiver 134. The right side transverse and thickness data is transmitted similarly via leads 136 and 138 for input to the transverse and thickness receivers 132 and 134. Left side longitudinal data from pulser/pre-amp 90 is conducted via line 140 through cable 14 for input to a longitudinal receiver 142, and right side longitudinal data from pulser/pre-amp 102 is communicated via lead 144 back to longitudinal receiver 142. Address buss data on line 106 is also applied to respective Trim Pot decoder circuits 146 and 148 which provide control outputs, respectively, to the transverse receivers 132 and 134, and the longitudinal receiver 142. Each of the receivers 132, 134 and 142 includes channel 1 and channel 2 inputs for left side and right side data respectively. The receivers amplify and rectify the incoming RF signals in selected sequence to provide a video output to thickness and amplitude analysis gate boards, as will be further described. The Trim Pot decoder 146, responsive to address buss 106, provides calibration input on leads 150 and 152 to the transverse receiver and thickness receiver, respectively. Similarly, Trim Pot decoder 148 provides calibration output on lead 154 to the longitudinal receiver 142. Video output from the receivers 132, 134 and 142 is present on respective leads 154, 156 and 158.

Referring now to FIG. 5, sequential transverse video data on lead 154 is applied to a transverse amplitude gate 160 as similar video outputs from leads 156 and 158 are applied to a thickness gate 162 and a longitudinal amplitude gate 164, respectively. Each of the transverse and longitudinal gates 160 and 164 consist of an identical type of peak amplitude detector, each of which is responsive in sequence to forty transducers, i.e. responsive to twenty pulser pre-amps with two transducers per pre-amp, to provide output of a gate pulse and an analog DC voltage corresponding to the maximum signal amplitude detected.

The thickness gate 162 contains four thickness channels that are actuated sequentially to detect a minimum detected thickness during a frame interval. At the end of the frame, the minimum thickness value is transferred to a sample and hold register for output of an analog signal proportional to the detected minimum thickness. Transverse amplitude gate 160 provides a transverse threshold voltage on lead 166 and a transverse indication on lead 168 for conduction to the interface and strip chart recorder 170. A flaw detection output is also applied on a lead 172 for input to a transverse counter 174. Interconnect 176 provides frame set and reset data between sequence controller 108 and transverse amplitude gate 160. The longitudinal amplitude gate 164 includes similar outputs of a flaw detect pulse output on lead 178 to a longitudinal counter 180, and a longitudinal threshold signal on lead 182 and longitudinal data output on lead 184 as both are applied to interface and strip chart 170. Frame set and reset data is applied from sequence controller 108 via lead 186.

The thickness gate 162 provides a thickness output on a lead 188 to a thickness alarm counter 190, and it also provides a TOO THIN output on lead 192 to a thickness warning counter 194. Thickness threshold and thickness voltage are output on respective leads 196 and 198 to the interface and strip chart 170, and frame set and reset is interconnected on line 200 from sequence controller 108. The thickness voltage output on lead 198 is also applied to a thickness meter 202 which may be such as a digital meter reading out thickness in thousandths of an inch.

The interconnects 204 between sequence controller 108 and each of the counters 174, 190, 194 and 180 control outputs and inputs as each of the counters functions as an averager board in very close functional relationship to the sequence controller 108. Thus, the counters can essentially be considered an extension of the operation control of the sequencer. Such functional operations include: Averaging counters; Averaging counters load point select switches; Driving the signal lines to the test head unit 12; Channel decoding of the programmable read only memory in sequence controller 108; Channel decoding to route selected control pulses to the gate circuits 160, 162 and 164; and, providing gate termination. Additional interconnects 206 connect each of the counters 174, 190, 194 and 180 to the alarm latch and drivers board 208 which, in turn, may provide selected outputs to alarms, annunciators, defect markers and the like (not specifically shown). Instantaneous operator surveillance may be aided by synch output from sequence controller 108 via line 210 to a monitor 212, an oscilloscope or similar recorder, that may receive selected video and timing inputs 214.

Referring now to FIG. 6, the pulser/pre-amp 84 is shown in greater detail including a plurality of twelve individual pulser pre-amp circuits as they receive input from select-trigger interconnection 110 and connect to the left transverse and thickness transducers 80 (FIG. 4) by means of the pulsing connections 82. Received transducer output from connections 82, and as processed in the individual pre-amplifiers, is then output through a diode bank and operational amplifier output to the leads 128 and 130 (cable 14) for conduction back to the control console 16. Thus, FIG. 6 represents but a single pulser/pre-amp 84 as utilized with the left transverse and thickness transducers 80 for control of 20 transverse transducers and two thickness transducers as an amplified thickness video output is sequentially generated through op-amp 220 for conduction on lead 130, while sequentially pulsed transverse transducer outputs are processed through op-amp 222 for output on lead 128.

The pulser/pre-amp 84 receives input from decoder 104 (FIG. 4) of twelve SELECT inputs 224 and twelve TRIGGER INPUTS 226 as generated in decoder 104 to sequence transducer pulsing. The pulser/pre-amp 84, includes a plurality of pulser pre-amp circuits 84-1, 84-2, 84-3 and so on to pulser pre-amp circuit 84-12. The pulser/pre-amp 84 is connected so that pulser pre-amps 84-1 and 84-2 control the left side thickness transducers and pulser pre-amps 84-3 through 84-12 control the left side transverse transducers. The pulser/pre-amp 96 would be similarly wired to handle the right transverse and thickness transducers 92 (see FIG. 4). A similar circuit board is utilized at pulser/pre-amp 90 and would be wired with only ten individual pulser pre-amp circuits to control the twenty left longitudinal transducers 86, and the pulser/pre-amp circuit board 102 would be similarly wired to control the right longitudinal transducers 98.

As previously stated, a preferred sequence of firing may be as follows:

| SEQUENCE | ACTIVE TRANSDUCERS |
|---|---|
| 1 | Thickness 1L |
| 2 | Thickness 2L |
| 3 | Thickness 3R |
| 4 | Thickness 4R |
| 5 | Transverse 1 and 11 |
| 6 | Transverse 2 and 12 |
| 7 | Transverse 3 and 13 |
| .. | .... |
| 14 | Transverse 10 and 20 |
| 15 | Transverse 21 and 31 |
| 16 | Transverse 22 and 32 |
| .. | .... |
| 24 | Transverse 30 and 40 |
| 25 | Longitudinal 1 and 11 |
| 26 | Longitudinal 2 and 12 |
| 27 | Longitudinal 3 and 13 |
| .. | .... |
| 34 | Longitudinal 10 and 20 |
| 35 | Longitudinal 21 and 31 |
| 36 | Longitudinal 22 and 32 |
| .. | .... |
| 43 | .... |
| 44 | Longitudinal 30 and 40 |

Each pulser pre-amp 84-n actuates a respective pulsing lead 82 which is connected in parallel to actuate a selected pair of transducers. Thus, in the case of pulser/pre-amp 84, pulsar pre-amp 84-1 is actuated to energize pulsing line 82-1 to fire the No. 1 left thickness transducer which returns signal energy processed through the pre-amp portion with output indication provided on lead 228 through a diode 230 for amplification in op-amp 220 and RF indication output on lead 130 to control console 16. In like manner, pulser pre-amp 84-2 energizes pulser line 82-2 to the remaining left thickness transducer and return energy is amplified with output on lead 232 through diode 234 and op-amp 220. As sequencing recommences through the left side transducers, SELECT and TRIGGER inputs actuate pulser pre-amp 84-3 to energize pulsing lead 82-3 and transverse transducers 1 and 11 with subsequent signal return amplified and output on a lead 82-3 through a respective diode 236-3 for output through op-amp 222 and RF lead 128 to control console 116. Thus, sequential energization of the pulser/pre-amps 84, 90, 96 and 102 function to effect transducer energization and received signal processing through all eighty-four transducers in the circumferential array.

FIG. 7 illustrates schematically an individual pulser pre-amp circuit, e.g. pulser pre-amp 84-1 and the attendant input and output connections. The pulser portion of the circuit centers around an SCR 240, Type GA301, having a common connected plate, a cathode connected to a junction 242 and having a gate electrode connected through a resistor 244 to the trigger input 226-1. The junction 242 is connected through a load resistor 246 to the +100 volt supply lead 118 as well as through a capacitor 248 and junction 250 to a tuned output circuit. The junction 250 is connected through a tuning coil 252 to the regulated +12 volt supply lead 124, and junction 250 is also connected to the plate of a diode 254 having its cathode connected to a junction 256 which provides parallel output through tuning resistors 258 and 260 to the pulsing leads 262 and 264, i.e. pulsing lead pair 82-1.

Thus, trigger input to SCR 240 develops a high voltage pulse at junction 242 to energize oscillation as developed at junction 256 to provide parallel pulsing output for energization of a select pair of transducers. Inductance 252 and capacitor 248 provide an L-C circuit for setting the frequency of oscillation. In present operation, the thickness transducers are pulsed at 5.0 MHz while the transverse and longitudinal transducers are each pulsed at a frequency of 2.25 MHz.

The return low level signal as received back from the transducers through junction point 256 on lead 266 for amplification in solid state amplifier 268, a Type 3N211, to provide a return signal output at a junction 270. The amplification factor of device 268 is controlled by the setting of trim potentiometer 272 connected between ground and the regulated 12 volt input. Passive elements, i.e. inductance 274 and common-connected capacitor 276, filter the low level received transducer signal as seen at junction 278 for input to selection and pre-amplification circuitry consisting of NPN transistors 280 and 282, Type 2N4401. Transistor 280 is connected with the collector energized by the 12 volt regulated supply on lead 124 and the input SELECT pulse on lead 224-1 is applied to the base. A positive-going signal on the base enables conduction of transistor 280 and energization of amplifier transistor 282 and transducer return signal present on the base (junction 270) is amplified to provide output transducer signal on lead 228. The inductance 274 and capacitance 276 will vary in accordance with the particular frequency of operation, i.e. selection at 2.7 MHz uses a 100 microhenry inductance and a 30 picafarad capacitance while operation at 5 MHz utilizes a 47 microhenry inductance and a 10 picafarad capacitance. The output signal on lead 228 is then applied through an output diode, e.g. 230 of FIG. 6, for input to the summing amplifier or op-amp 220 and output on lead 130. The summing operational amplifiers serve to drive the amplified return signal over the extended length cable 14 to the receiver units at the control console.

Figure 8:
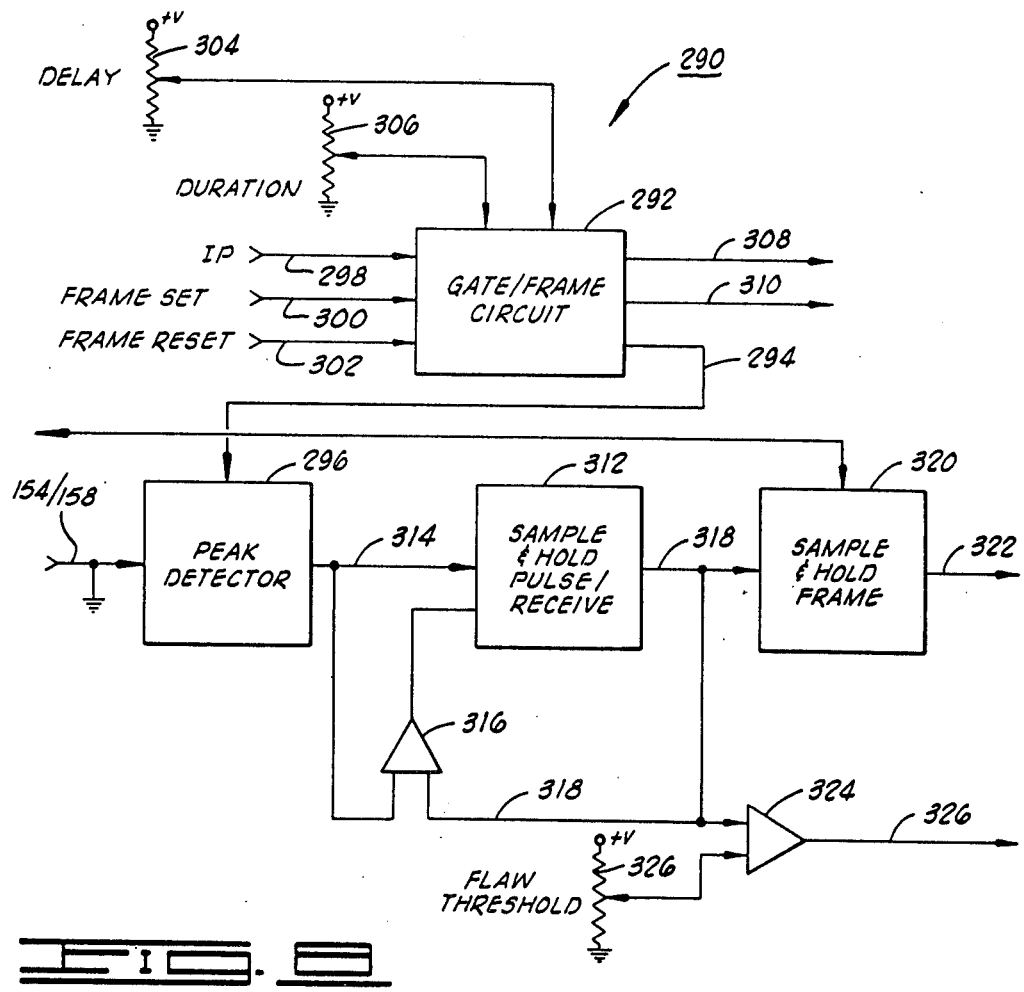
FIG. 8 is a block diagram of an amplitude gate circuit as shown in FIG. 5.
Figure 9:
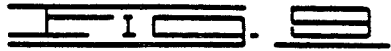
FIG. 9 is a graphic representation of pulse/time relationships of pulses operative in the amplitude gate of FIG. 6.

FIG. 8 is an amplitude gate circuit 290 which may be either the transverse amplitude gate 160 or longitudinal amplitude gate 164 of FIG. 5. A gate/frame generation circuit 292 provides a gate output on lead 294 to a peak detector 296 which also receives input of video signal from the transverse (or longitudinal) receiver on lead 154 (or 158). The gate/frame circuit 292 receives input of IP (initial pulse) signal on lead 298, frame set input on lead 300 and frame reset input on lead 302 as the frame pulse sets the period of time in which 40 transducers or 20 pulser pre-amp energizations (two transducers per pre-amp) take place. Referring also to FIG. 9, the IP, frame and gating pulses are illustrated in pulse-width versus time relationship. The gate/frame circuit 292 is statically controlled as to gate delay and gate duration by voltage divider potentiometers 304 and 306, respectively, and gate marker and gate done outputs are provided on respective leads 308 and 310 to the interface of the strip chart and other display apparatus as shown in FIG. 5.

Each time a transducer group is fired, as initiated by an IP pule within its frame, a gate signal is output on lead 294 after a predetermined gate delay as determined by potentiometer 304. Video or transducer return signal is also present on input lead 154 (or 158) to peak detector 196, and the peak detector outputs an analog signal that is directly proportional to the largest amplitude of any signal input to peak detector 296 during the duration of gate input on lead 296. At the close of gate, or during the gate done pulse period, the amplitude detected by the peak detection circuitry is compared with the output of the first sample and hold circuit 312. Thus, output from peak detector 296 is applied on line 314 to both the sample and hold circuit 312 and one input of a peak amplitude comparator 316, as output from the sample and hold 312 on lead 318 is also applied to the amplitude comparator 316. The output on lead 318 is also input to a second sample and hold circuit 320 which functions to hold signal for an entire frame duration.

Thus, the peak amplitude comparator 316 compares amplitude of successive peak samples as detected in successive gates within peak detector 296. When the output on lead 318 is lesser, the sample and hold circuit 312 again samples the larger peak value and holds it for the next comparison through peak amplitude comparator 316. The first pulse/receive cycle, i.e. an IP signal duration, always results in a sampling since the peak detector 296 and sample and hold 312 are cleared at the beginning of each frame. As new measurements are made within a frame, the sample and hold 312 is activated whenever the new incoming measurement from peak detector 296 exceeds the held peak from a previous sample. The process then continues until the last sample reading is obtained within that particular frame duration. At the close of the frame duration, the pulse value held in sample and hold 312 in output to sample and hold circuit 320 for output via lead 322 to the strip chart and other display indicators. A threshold comparator 324 receives input from first sample and hold circuit 312 for comparison with a flaw threshold input as derived from a voltage divider potentiometer 326, and a comparator output on a lead 326 to the control sequencer 108 (FIG. 5) indicates that the threshold comparisons are valid at the close of frame.

Figure 10:
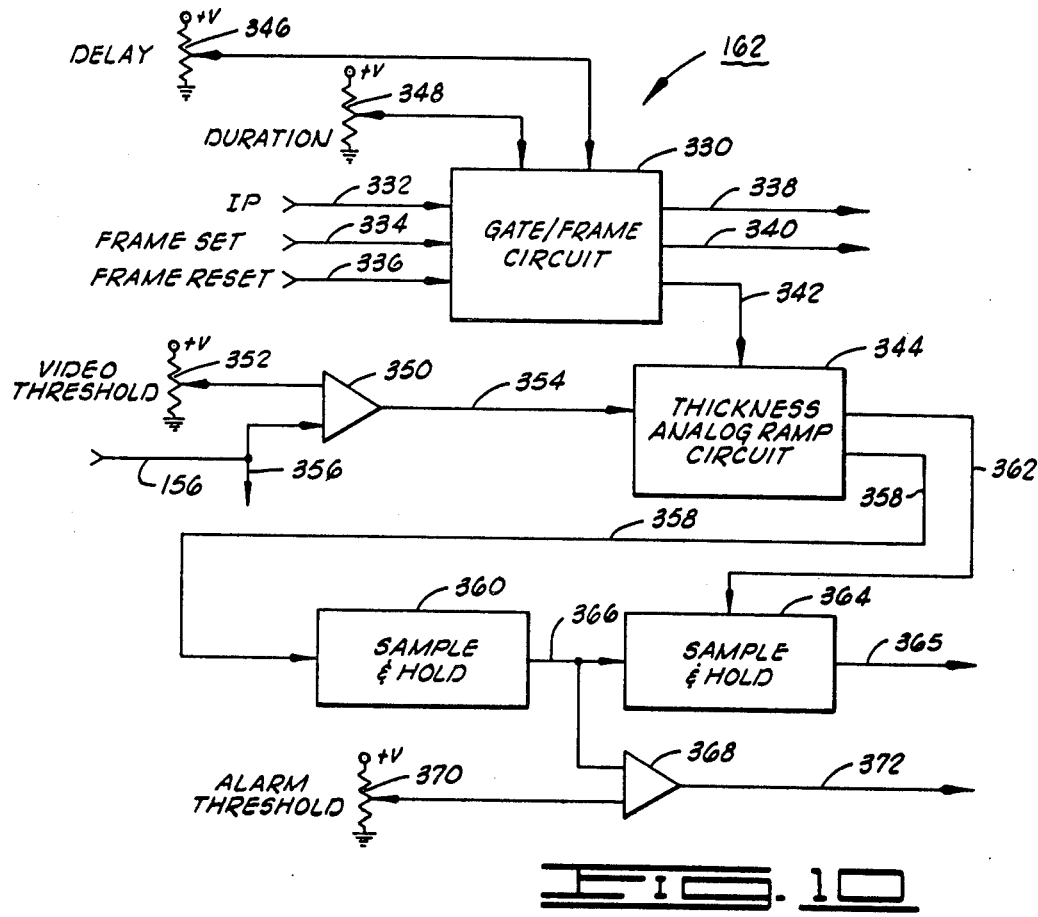
FIG. 10 is a block diagram of a thickness gate circuit as used in the circuitry of FIG. 5.
Figure 11:
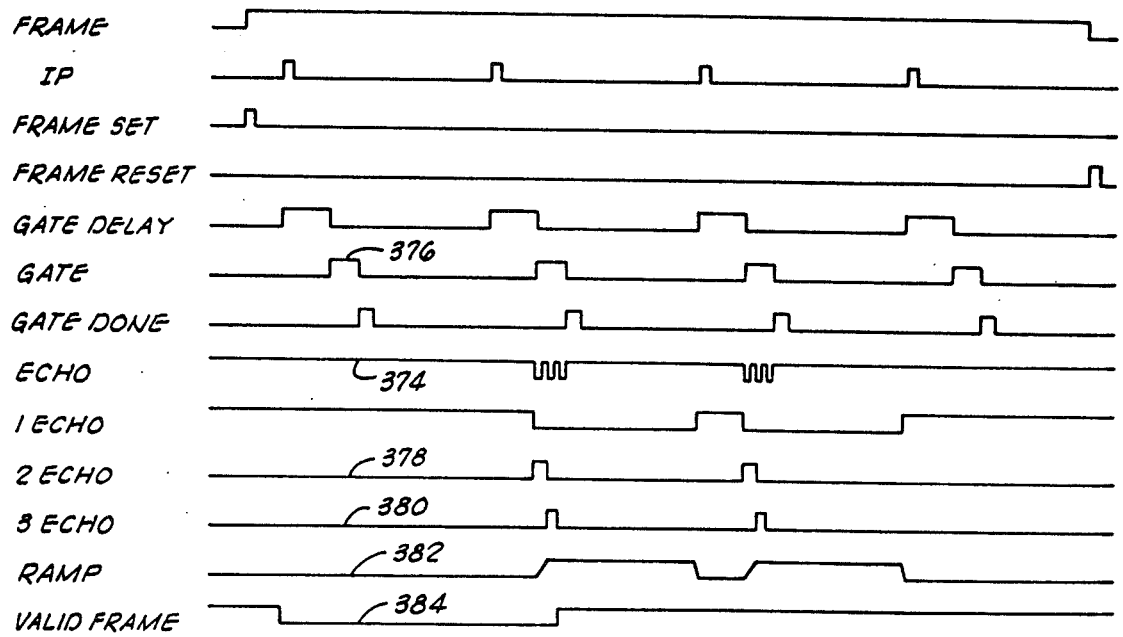
FIG. 11 are graphic pulse/time representations of signals operative in the thickness gate of FIG. 10.

FIGS. 10 and 11 illustrate in greater detail the thickness gate 162 and the various pulse/time relationships contributing to its function. The thickness gate 162 also functions under control of a gate/frame circuit 330 as it receives input of IP, frame set and frame reset pulse voltage on respective leads 332, 334, and 336, and gate marker and gate done outputs are provided on leads 338 and 340 as output gate pulse is applied via line 342 to a thickness analog ramp circuit 344. Gate delay and gate duration are controlled by inputs from the voltage divider potentiometers 346 and 348.

Video input from thickness video lead 156 (FIG. 5) is applied to a threshold comparator 350 which receives threshold standard input from a voltage divider potentiometer 352 as the compared video signal is output on lead 354 to the thickness analog ramp circuit 344. A video output 356 is also provided for direct connection to the interface and video display monitor. Output from ramp circuit 344 via lead 358 is applied to a sample and hold circuit 360 which functions to retain a thinnest thickness value detected during a frame duration, and a ramp output 362 is applied to a second sample and hold circuit 364 as it also receives input from sample and hold circuit 360 via connection 366. The connection 366 is also applied to a threshold comparator 368 for comparison to a voltage as set by a voltage divider potentiometer 370, and an alarm output is applied on lead 372 for thickness flaw detection indication.

The gate/frame circuit 330 functions on thickness frame timing from the sequence controller 108, via connection 200 (FIG. 5), so that the four thickness channels are activated in sequential and cyclical manner. Within each thickness frame cycle, the four transverse transducers are activated and return signal is monitored via thickness gate 162 to detect and store the minimum detected thickness. At the end of the frame, the minimum thickness value is transferred to a sample and hold register consisting of sample and hold circuits 360 and 364 which function to output an analog signal proportional to the detected minimum thickness via lead 365 to the strip chart recorder as well as to other display apparatus.

For a number of reasons, there occur instances where the tubular goods does not allow the gate to successfully measure thickness, this is particularly true of drill pipe. In such cases, the derived measurement for thickness is either zero or infinite thickness and such false readings pose objectionable clutter on the strip chart recorder and interfere with interpretation. The two most common errors are (1) failure to detect any echos from the pipe, and (2) detecting the front surface echo but not the rear surface echo, and it is desirable to detect and compensate for such errors to improve significantly the thickness measurement operation. Both of the above conditions are automatically detected by monitoring for presence of two separate signals within an allotted time window and failure to satisfy the condition signifies that a failure has occurred.

The sample and hold 360 is used to store a thickness detected at any point within a frame while the sample and hold circuit 364 is used to store an updated minimum thickness that is detected anywhere within the valid frame pulse duration. Thus, for each pulse/receive function, i.e. transducer firing as per the IP pulse and reception of the return signal, the circuit monitors for the presence of at least two distinct echo signals within a designated time window. As shown in FIG. 11, a valid thickness may be derived from such as echo pulse 374 which exhibits a plurality of return peaks within the duration of gate 376 as actual thickness measurement is made between the two echo and three echo pulses 378 and 380. This is indicated by the duration of pulse rise in ramp pulse 382. A valid frame pulse 384, as present on lead 362 (FIG. 10), signifies a valid thickness reading as the thickness output indication is applied on lead 358 to sample and hold 360. Sample and hold 360 stores the first valid thickness reading after the beginning of a new frame, and sample and hold 360 is re-activated with a new thickness measurement whenever the new thickness is thinner than the previous measurement within that given frame. This process continues through the thickness frame and, after the last measurement is made, decision is made to transfer the content of sample and hold 360 to the sample and hold 364. The decision occurs if at least one valid measurement was made during the frame whereupon sample and hold 364 is updated to the current value, but if no valid measurement was made during the frame a fault indication is activated.

FIG. 12 illustrates the clock circuitry of the sequence controller 108 (FIG. 5). Basic clock frequency of 6 MHz is output from an oscillator 390, a type S14R2, through series connected quad flip-flops 392 and 394, type 74C175 and 14175, respectively. The 6 MHz output from oscillator 390 is also applid through a series of decade counters 396, 398 and 400, each type 74C162, as 6 KHz output is available on line 402 for input to multivibrator 404, a dual mono-stable multivibrator type 14528, which provides synch clock output on a lead 406. An output from the second decade counter 398 on lead 408 to a quad flip-flop 410, type 14175, provides a 10 KHz output via line 412 to the multivibrator 404 as the inputs 412 and 402 may be selectively applied to energize multivibrator 404 thereby to adjust the frequency of synch clock output on lead 406.

Output from quad flip-flop 394 is applid on lead 414 through an inverter 416 to provide 1 MHz output on lead 418. Output from quad flip-flop 394 is also applied through a NOR gate 420 to provide PROM clock output on lead 422, and flip-flop output on lead 424 through AND gate 426 and OR gate 428 provides output of register clock pulse on lead 430 as PROM clock is parallel input through OR gate 428. Thus, the clock circuitry divides the basic oscillator output to derive the various repetition rates which are used in determining the firing rate of the pulser/pre-amps in the transducer head as well as the analysis rate of the thickness gates and the detection circuitry. The PROM clock, register clock and 1 MHz pulse outputs on respective leads 422, 430 and 418 are all utilized to control operation of the sequence controller 108 (FIG. 5) and the averager counter circuitry functioning in coaction therewith.

FIG. 13 illustrates the control processor circuit 440 of sequence controller 108 (FIG. 5) which functions to provide the system program and address control. PROM clock on lead 422 is input from the clock circuitry and applied in parallel to each of a plurality of EPROMs 442, 444, 446 and 448, type IM6654 Eraseable Programmable Read-Only Memories. 1 MHz clock input on lead 418 is then applied in parallel to each of binary counters 450, 452 and 454, each type 74C163 binary counter with synch clear. Register clock input on lead 430 is applied as input to clock each of octal flip-flops 456, 458 and 460, each type 74374 octal D-type flip-flop.

Outputs 1-4, 5-8 and 9 on multi-lead connector 462 from respective binary counters 450, 452, 454 are applied as inputs 1-9 in parallel to each of the EPROMs 442-448. Outputs 1-8, 9-16, 17-24 and 25-30 from respective EPROMs 442, 444, 446 and 448 are output on multi-lead connector 464 for input to various terminal interconnections as follows: 14-21 to octal flip-flop 456, wires 22-29 to octal flip-flop 458, connections 30-32 to octal flip-flop 460, connection 9 to binary counter 454, connections 5-8 to binary counter 452, connections 1-4 to binary counter 450, and connections 10-13 are connected in parallel to each of multiplexers 466 and 468, type 74C151 eight channel digital multiplexers. The multiplexer 466 is initiated with input of synch clock on lead 406 to provide an output through OR gate 470 to provide output on lead 472 to the LD input (load) of respective binary counters 450-454.

Functionally, the control processor 440 is divided into four basic sections: the control PROM set consisting of EPROMs 442-448, the program counter as made up of binary counters 450-454, the condition code selector consisting of multiplexers 466 and 468, and the control registers as performed by octal flip-flops 456-460. The control processor 440 is a semiintelligent programmable sequencer wherein the control PROM set contains the software encoded to implement the three different modes of operation, i.e. calibration, run, and self-test. The program counters 450-454 maintain the address of the current program step as the counter can either be incremented to the next location, jumped to another location supplied by the control PROM set, or be cleared to zero, i.e. the master reset condition. The condition code selectors or multiplexers 466, 468 select one of sixteen available code inputs to be routed through OR gate 470 to the load input of the program counters 450-454. If input is low, the counters 450-454 will be loaded with address supplied by the EPROMs 442-448 to effect a jump to the program address supplied by the encoded program. The EPROMs 442-448 control the condition code selection and even the loading, to the extent that two of the condition code inputs can cause the program to always jump or to never jump, i.e. to continue.

The control register or flip-flops 456-460 along with a control strobe selector or decoder 474, a type 14556 dual binary to 1-of-4 decoder (inverting), provide signals at appropriate times to implement the various modes of operation as they ecode control bits as provided from the EPROMs 442-448 via multi-lead connector 464. Control strobe decoder 474 is controlled by binary output on a multi-lead connector 476 from flip-flop 458 which provides control strobe outputs 0, 1 and 2 for input in dual mode to each decoder half of the dual binary decoder 474. Thus, in accordance with binary control strobe coding, the decoder 474 will output longitudinal, transverse and thickness reset strobe pulses 478 and frame set and reset and average counter load pulses on leads 480 along with initial and synch pulse outputs 482.

Output control bits from the EPROMs 442-448 are divided into 32 designated bits as applied out on multi-lead connector 464. A first field of bits 1-9 from connector 464 is the program jump address field which is routed to the program counters 450-454. A next field of bits 10-13 from connector 464 are applied to the multiplexers 466 and 468 to control the multiplexer code condition which provides the decision to the program counter 450-454 as to whether or not to jump operation. Bit 14 is routed through flip-flop 456 as the Active output which is applied to the main and remote alarm panel to indicate status of the sequencer. The next four bits 15-18 provide averager count control as well as direction and enabling of the averager counters. The next 6 bits 19-24 through flip-flops 456 and 458 provide transducer address line outputs TADD 0-TADD 5 which supply the channel PROM address inputs in the run or operational mode of the system. The next two bits 25 and 26 are available for expansion and bits 27-29 through flip-flop 458 are designated as the control strobe bits which control mutually exclusive events of the inspection system through binary coded activation of the dual decoders 474.

FIG. 14 illustrates the address random access memory 490 of the sequence controller. Transducer address input TADD 0-TADD 5, as output from flip-flops 456 and 458 (FIG. 13), are input on a multi-lead connector 492 for input in parallel to each of multiplexers 494 and 496, type 74C157 Quad 2-input multiplexers. Front panel thumb wheel switches 498 and 500 provide binary output input of least significant and most significant digits for input to a random access memory 502, type 74184. Outputs from the memory 502 as well as the $b_0$ output on lead 504 from LSD switch 498 are applied to parallel channels of a buffer 506, a type 74C906 Hex Open Drain N-channel buffer, with output applied via the multi-lead connector 508 for parallel input to each of multiplexers 494 and 496. The multiplexers 494 and 496 are enabled by operating mode input on a lead 510 from front panel control, and multiplexers 494 and 496 then output coded address data A0-A5 on a multi-lead connector 512.

Referring now to FIG. 15, the connector 512 with address data A0–A5 along with synch signal from lead 482 (FIG. 13) is applied in parallel to each of dual differential line drivers 514, 516, 518 and 520, type 78C30. Each of line drivers 514–520 then provides differential output for successive address data inputs. That is, line driver 514 provides dual outputs A0+, A0− and A1+, A1− onto multi-lead connector 522, line driver 516 outputs A2+, A2−, and A3+, A3−, driver 518 outputs A4+, A4− and A5+, A5−, and line driver 520 outputs synch+ and synch−. The differential driver section converts the level of the address and synch lines to improve signal drive over extended cable length to the head unit.

The remainder of FIG. 15 constitutes the averager circuitry which functions coactively with sequence controller 108 and also includes the FIG. 5 block designations of transverse counter 174, thickness alarm counter 190, thickness warning counter 194 and longitudinal counter 180. Each averager counter is made up of two binary up-down counters of eight bit wide type as programmed by binary coded input from respective dip switches. The binary up-down counters are each of type 14516B. Counters 524 and 526 function as the thickness alarm averaging counter as programmed by dip switch 528 via eight-bit connector 530 which provides four-bit coded input to each of counters 524 and 526 as well as four-bit input to each of four-bit comparators 532 and 534 (see FIG. 16). The four-bit comparators are type 14585B four bit magnitude comparators. Binary counter 524 receives CL input through a NAND gate 536 from a type 14556B dual binary to 1-4 decoder 538 which provides enabling voltage outputs for each of thickness, transverse, longitudinal and thickness warning channels in response to input of average count pulses from octal flip-flop 456 (FIG. 13).

Thus, when output from binary decoder 538 enables through NAND gate 536 to the thickness alarm counters 524 and 526, the counter will increment in response to receipt of a flaw indication, and will attempt to decrement by two in response to a no flaw condition. However, when the four-bit comparators 532 and 534 detect that the output of counters 524 and 526 is equal to the load value of dip switch 528, an output is generated on line 540 from comparator 534 (FIG. 16) and applied to NAND gate 536 to disable the binary up-down counter 524. This prevents the up-down counter from being decremented past the load point thereby to allow consistent averaging of any flaws. Generally, the normal condition will be when no flaw exists and the average counters will then remain at the load points; and, when a flaw is encountered the counters are incremented once per frame. When the counter reaches its terminal count (e.g. 255), the alarm signal is activated via lead 541 and latched on the interface board to generate an alarm condition. Counters are reset to the switch load point by front panel operator reset.

Similar operation of averaging count is effected for each of the transverse alarm, longitudinal alarm and thickness warning conditions. Thus, a dip switch 542 functions with binary up-down counters 544 and 546 to carry out transverse defect averaging when enabled by a respective NAND gate 548. Dip switch 542 provides transverse eight-bit data on lead 549 both to the counters 544 and 546 and to a pair of four-bit comparators 550 and 552. Output binary data from counters 544 and 546 via lead 554 is also applied to comparators 550 and 552 with subsequent load point output on a lead 556 for the purpose of disabling the respective NAND gate 548. Transverse alarm is output on lead 557 after the load point count. A resistor network 558 provides bias equalization as between the code inputs to each of the thickness comparators 532, 534 and the transverse comparators 550 and 552.

Referring again to FIGS. 15 and 16, the same identical circuitry serves the averaging function for the longitudinal alarm and thickness warning conditions as each is enabled from output of binary decoder 538 in sequence. Thus, the longitudinal flaw averaging is effected by binary up-down counters 560 and 562 as coded by dip switch 564 and actuated by enablement of NAND gate 566. Binary outputs from counters 560 and 562 are compared in four bit comparators 568 and 570 with disable signal applied on a lead 572 to NAND gate 566 as longitudinal alarm is output on lead 573. The same identical connection applies for the thickness warning condition on lead 575 utilizing dip switch 574, binary up-down counters 576, 578, enabling NAND gate 580 and four bit comparators 582, 584. Disabling signal is returned from the comparator circuitry (FIG. 16) via lead 586 to one input of NAND gate 580.

A channel selector 590, type 14529BAL dual four channel analog data selector, is switched by average count 0 and 1 inputs from octal flip-flop 456 (FIG. 13) as applied on connector 592 to provide alarm output 594 in response to inputs from thickness alarm input 531, transverse alarm input 557, longitudinal alarm input 573, or thickness warning input 575. Frame set and frame reset pulses are applied into a binary decoder 594, a type 14555B dual binary to 1 of 4 decoder, which also receives control actuation from connector 592 to provide outputs 596 that consist of frame set pulses for thickness, transverse and longitudinal operation and frame reset pulses for thickness, transverse and longitudinal operation. Finally, a binary decoder 598, also type 14555B, receives initial pulse input to provide each of thickness, transverse and longitudinal initial pulse outputs 600.

The foregoing discloses a novel ultrasonic testing system that is capable of testing tubular goods, particularly oil field pipe and casing, with greater speed and reliability. The system includes a control console, extensive connector cable, and test head, and the selection and arrangement of component structure enables the test head to be stationarily diposed at a considerable distance from the control console and operator position. In addition, the test head carries out full circumphery testing for longitudinal and transverse defects, non-rotatively, at relatively high speed linear movement along the tubular goods. The circuitry tests for each of longitudinal and transverse defects and for wall thickness, and defect or flaw indications are averaged over selected durations to verify type and size of defect while also removing clutter and generally clarifying output data data displays and read-out.

Changes may be made in combination and arrangement of elements as heretofore set forth in the specification and shown in the drawings; it being understood that changes may be made in the embodiments disclosed without departing from the spirit and scope of the invention as defined in the following claims.

What is claimed is:

1. An ultrasonic testing system for tubular goods, comprising:

a plurality of ultrasonic transducers disposed in at least one circumferential array for energy-coupled disposition concentric to said tubular goods;

a plurality of pulser means for pulsing a selected at least one of said transducers in a predetermined serial order and receiving respected flaw-induced return signal outputs;

plural amplifying means that are enabled serially to receive input of said return signal outputs to generate respective data signals;

sequence controller means responsive to stored program and generating an address data output for sequence control of said plurality of pulser means and plural amplifying means;

decoder means responsive to said address data output to enable energization of a selected pulser means and a counterpart amplifying means;

receiver means receiving inputs of said respective data signals and generating successive data outputs;

gate means receiving inputs of said data outputs to provide peak detected output signals having amplitudes proportional to a defect magnitude; and means responsive to said peak detected output signals to indicate defects in said tubular goods.

2. A system as set forth in claim 1 wherein said plurality of ultrasonic transducers comprise:

a first plurality of transducers which are each oriented at a first acute angle relative to the radius of the tubular goods for detection of transverse defects; and a second plurality of transducers which are each oriented at a second acute angle relative to the radius of the tubular goods for detection of longitudinal defects.

3. A system as set forth in claim 2 wherein said receiver means comprises:

first receiver means receiving inputs of data signals from said first plurality of transducers to generate first data outputs; and second receiver means receiving inputs of data signals from said first plurality of transducers to generate second data outputs.

4. A system as set forth in claim 3 wherein said gate means comprises:

first gate means receiving said first data output and producing first peak detected output signals; and second gate means receiving said second data output and producing second peak detected output signals.

5. A system as set forth in claim 4 which is further characterized to include:

first averager means outputting a first alarm signal in response to a predetermined number of consecutive first peak detected output signals; and second averager means outputting a second alarm signal in response to a predetermined number of consecutive second peak detected output signals.

6. A system as set forth in claim 5 which further includes:

a plurality of ultrasonic thickness transducers disposed in said array and secured in radial alignment to said tubular goods;

means for pulsing said thickness transducers and amplifying the thickness signal output;

thickness receiver means receiving said thickness signal output and generating a thickness data output; and gate means receiving said thickness data output to generate a pulse output indicative of wall thickness of the tubular goods.

7. A system as set forth in claim 1 which further includes:

a plurality of ultrasonic thickness transducers disposed in said array and secured in radial alignment to said tubular goods;

means for pulsing said thickness transducers and amplifying the thickness signal output;

thickness receiver means receiving said thickness signal output and generating a thickness data output; and gate means receiving said thickness data output to generate a pulse output indicative of wall thickness of the tubular goods.

8. A system as set forth in claim 7 wherein said plurality of ultrasonic transducers comprise:

a first plurality which are each oriented at a first acute angle relative to the radius of the tubular goods for detection of transverse defects; and a second plurality which are each oriented at a second acute angle relative to the radius of the tubular goods for detection of longitudinal defects.

9. A system as set forth in claim 1 wherein said plurality of ultrasonic transducers comprise:

a first circumfery of transducers each aligned at an acute angle relative to the radius of the tubular goods and lying within a plane common to the axis of the tubular goods, said transducers providing total coverage of a first circumferential area of said tubular goods;

a second circumfery of transducers each aligned at an acute angle relative to the radius of said tubular goods and lying within a plane normal to the axis of the tubular goods, said transducers providing total coverage of a second circumferential area of said tubular goods; and a third plurality of transducers each aligned radially to the tubular goods, said transducers being spaced around said tubular goods.

10. A system as set forth in claim 1 which is further characterized to include:

threshold comparator means receiving said peak detected outputs signals and providing further outputs to said means to indicate only if the peak detected output signals exceed a predetermined threshold voltage.

11. A system as set forth in claim 10 which is further characterized to include:

averager means outputting an alarm signal in response to a predetermined number of consecutive peak detected output signals.

12. A system as set forth in claim 1 which is further characterized to include:

averager means outputting an alarm signal in response to a predetermined number of consecutive peak detected output signals.

13. A system as set forth in claim 12 which is further characterized in that:

said sequence controller means provides timing control outputs to each of said gate means and said averager means.

14. A system as set forth in claim 13 wherein said averager means comprises:

up-down counter means strobed by said sequence controller means and outputting an alarm signal after a preset count of successive peak detected signals.

* * * * *